US00PP10542P

United States Patent [19]

DeClercq

[11] Patent Number: Plant 10,542

[45] Date of Patent: Aug. 4, 1998

[54] SPATHIPHYLLUM PLANT NAMED 'HIMALAYA'

[75] Inventor: Danny DeClercq, Destelbergen, Belgium

[73] Assignee: Milestone Agriculture, Inc., Apopka, Fla.

[21] Appl. No.: 842,061

[22] Filed: Apr. 23, 1997

[51] Int. Cl.[6] ..... A01H 5/00

[52] U.S. Cl. ..... Plt./88.1

[58] Field of Search ..... Plt./88.1

*Primary Examiner*—James R. Feyrer
*Attorney, Agent, or Firm*—C. A. Whealy

[57] ABSTRACT

A distinct cultivar of Spathiphyllum plant named Himalaya, characterized by its compact plant habit; moderate vigor; rapid growth rate; large dark green leaves are held horizontal to the petiole; early flowering; numerous large white flowers that are positioned just above the foliage on strong and erect peduncles; and long-lasting flowers.

1 Drawing Sheet

The present invention relates to a new and distinct cultivar of Spathiphyllum plant, botanically known as Spathiphyllum, and hereinafter referred to by the cultivar name Himalaya. The new Spathiphyllum will be marketed under the name Ann-Marie.

The new cultivar is a product of a planned and controlled breeding program conducted by the inventor in Lochristi, Belgium. The objective of the breeding program is to create new Spathiphyllum cultivars with good plant form, early flowering and large flowers. The new cultivar originated from a deliberate cross by the inventor between the propietary Spathiphyllum selection SP 7A as the female or seed parent and the proprietary Spathiphyllum selection SP 8 as the male or pollen parent. The cultivar Himalaya was discovered and selected by the inventor as a plant within the progeny of the stated cross in a controlled environment in Lochristi, Belgium. The new Spathiphyllum is more compact than either parent selection.

Asexual propagation of the new cultivar, by tissue culture, at Lochristi, Belgium, has shown that the unique features of this new Spathiphyllum plant are stable and reproduced true to type in successive generations of asexual propagation.

The new Spathiphyllum has not been observed under all possible environmental conditions. The phenotype may vary somewhat with variations in environment such as temperature and light intensity, without, however, any variance in genotype. The following observations, measurements and comparisons describe plants grown in Apopka, Fla., under commercial greenhouse conditions.

The following traits have been repeatedly observed and are determined to be the unique characteristics of Himalaya. These characteristics in combination distinguish Himalaya as a new and distinct cultivar:

1. Compact plant habit.
2. Moderate vigor, rapid growth rate.
3. Large dark green leaves that are held horizontal to the petiole.
4. Early flowering.
5. Numerous large white flowers that are positioned just above the foliage on strong and erect peduncles.
6. Long-lasting flowers.

The accompanying colored photograph illustrates the overall appearance of the new cultivar, showing the colors as true as it is reasonably possible to obtain in colored reproductions of this type. The photograph comprises a side perspective view of a typical potted plant of Himalaya.

In the following description, color references are made to The Royal Horticultural Society Colour Chart except where general terms of ordinary dictionary significance are used.

Botanical classification: Spathiphyllum cultivar Himalaya.

Parentage:

*Female parent.*—Proprietary Spathiphyllum selection SP 7A.

*Male parent.*—Proprietary Spathiphyllum selection SP 8.

Propagation: By division or by tissue culture.

*Time to initiate roots.*—Winter: About 10 days at 20° C. Summer: About 5 days at 26° C.

*Rooting habit.*—Freely branching, numerous fleshy roots.

Plant description:

*Plant shape.*—Upright, inverted triangle, symmetrical.

*Growth habit.*—Erect when young, becoming outwardly arching as leaves develop. Numerous side shoots give plants a full, dense appearance. Compact, appropriate for 10 to 15-cm containers.

*Plant height.*—About 25 cm from soil level to top of leaf plane.

*Plant vigor.*—Moderate vigor, rapid growth rate.

*Crop time.*—During the summer, 26° C. production temperatures, about 84 days are required to produce a 10-cm plant. During the winter, 20° C. production temperatures, about 112 days are required to produce a 10-cm plant.

*Foliage description.*—Leaf shape: Lanceolate. Leaf length: About 21 cm. Leaf width: About 12.5 cm. Margin: Entire. Leaf surface: Flat, rugose. Leaf tip: Acuminate. Leaf base: Obtuse. Leaf aspect: Mature leaves held perpendicular to petiole. Leaf texture: Leathery, smooth, glabrous, durable. Leaf color: Young, top side: 147A. Young, under side: 147B. Mature, top side: 147A. Mature, under side: 147B. Venation: Top side: 147A, sunken. Under side: 147B, prominent. Petiole length, primary shoots: About 20 cm. Petiole diameter, primary shoots, just below geniculum: About 3 mm. Geniculum diameter, primary shoots: About 4.5 mm. Petiole wing, primary shoots: Apparent on lower 90% of mature leaf petiole. Petiole color: Young: 144A. Fully developed: Winged area: 137A. Above winged area: 146A. Geniculum: 146A.

Flower description:

*Flower arrangement.*—Large concave spathe with spadix held 5 to 15 cm above the foliage. Numerous flowers arise from leaf axils.

*Flower longevity.*—Flowers are long-lasting, generally maintaining white color for about 12 weeks on the plant depending on light and temperature levels.

*Spathe.*—Shape: Ovate, lanceolate. Size: Length: About 17.5 cm. Width: About 10 cm. Aspect: Concave, curving over the spadix. Color: Before unrolling: White, 155D. Open flower: White, 155D, with green, 146A, adaxial midvein.

*Spadix.*—Size: Length: About 5.7 cm. Diameter: About 1.2 cm. Color: White. Pollen: White, abundant.

*Peduncle.*—Aspect: Strong and erect. Size: Length: About 33 cm. Diameter: About 5 mm. Color: 146A above winged area.

Disease resistance: No known Spathiphyllum diseases observed to date on plants grown under commercial greenhouse conditions.

Seed development: Seed development has not been observed.

It is claimed:

1. A new and distinct cultivar of Spathiphyllum plant named Himalaya, as illustrated and described.

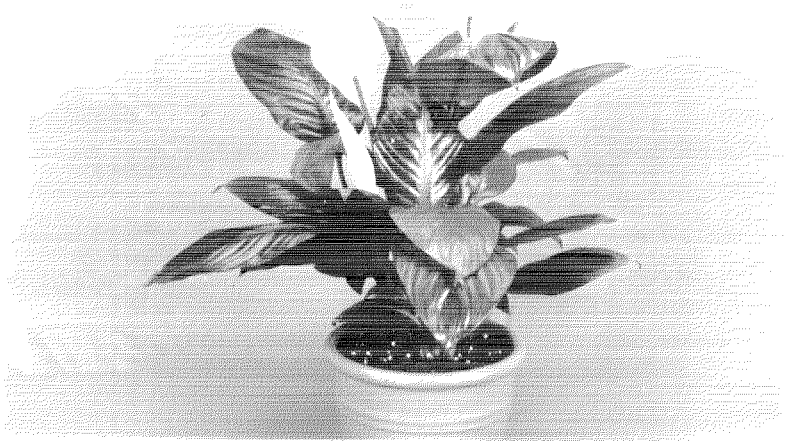

* * * * *